United States Patent
Cazaux et al.

(10) Patent No.: US 9,126,919 B2
(45) Date of Patent: Sep. 8, 2015

(54) USE OF MERCAPTO-METHYL ESTERS AS CHAIN TRANSFER AGENTS

(71) Applicant: Arkema France, Colombes Cedex (FR)

(72) Inventors: Jean-Benoit Cazaux, Lyons (FR); Pascal Saint-Louis-Augustin, Billere (FR); Georges Fremy, Sauveterre de Bearn (FR)

(73) Assignee: ARKEMA FRANCE, Colombes Cedex (FR)

( * ) Notice: Subject to any disclaimer, the term of this patent is extended or adjusted under 35 U.S.C. 154(b) by 0 days.

(21) Appl. No.: 14/179,855

(22) Filed: Feb. 13, 2014

(65) Prior Publication Data

US 2014/0235807 A1    Aug. 21, 2014

Related U.S. Application Data

(60) Provisional application No. 61/765,058, filed on Feb. 15, 2013.

(30) Foreign Application Priority Data

Feb. 15, 2013   (FR) ...................................... 13 51312

(51) Int. Cl.
*C08F 2/00* (2006.01)
*C08F 4/00* (2006.01)
*C07C 53/00* (2006.01)
*C07C 53/126* (2006.01)
*C08F 2/22* (2006.01)
*C08F 2/38* (2006.01)
*C08F 220/18* (2006.01)

(52) U.S. Cl.
CPC ................. *C07C 53/126* (2013.01); *C08F 2/22* (2013.01); *C08F 2/38* (2013.01); *C08F 220/18* (2013.01)

(58) Field of Classification Search
CPC ............. C08F 2/22; C08F 2/38; C08F 20/126
USPC .................... 526/214, 224; 554/101
See application file for complete search history.

(56) References Cited

U.S. PATENT DOCUMENTS 5,354,800 A * 10/1994 Suzuki et al. ................. 524/460

* cited by examiner

*Primary Examiner* — William Cheung
(74) *Attorney, Agent, or Firm* — Smith, Gambrell & Russell, LLP

(57) ABSTRACT

Disclosed herein is a chain transfer agent in a free-radical emulsion polymerization process, of at least one mercapto-methyl ester, and also relates to the free-radical emulsion (co)polymerization process comprising at least one such mercapto-methyl ester and uses thereof. Also disclosed herein are mercapto-methyl diesters.

16 Claims, No Drawings

USE OF MERCAPTO-METHYL ESTERS AS CHAIN TRANSFER AGENTS

The subject of the invention is mercapto-methyl esters of carboxylic acids, and the process for preparing same. The invention also relates to the use of said mercapto-ester derivatives as a chain transfer agent in free-radical emulsion (co) polymerization reactions, and to the free-radical emulsion (co)polymerization processes using said mercapto-methyl esters of carboxylic acids as chain transfer agents.

The intrinsic characteristics of polymers, such as the average size of the chains and their distributions have strong influences on the macroscopic properties of the resulting materials. Indeed, the properties of a polymer, in particular in solution or in the molten state, such as the viscosity, are greatly dependent on its molar mass and on its polymolecularity index. As a general rule, the lower the molar mass of a polymer and the narrower its distribution, the lower the viscosity of said polymer. A low viscosity is generally sought in forming applications, for example by injection-molding or extrusion of polymer.

When in the form of an emulsion, latex and the like, for example in coating and adhesive applications, polymers having a narrow molar mass distribution are preferred. Such polymers with a narrow molar mass distribution are generally prepared in the presence of a chain transfer agent (or more simply "transfer agent", or else "CTA").

The use of a transfer agent makes it possible to obtain a more homogeneous polymer particle size and also increased stability, in comparison with a polymer prepared without transfer agent. This increased stability allows better resistance during the various storage, pumping and transporting operations, and also improved compatibility of polymer emulsions, during formulation processes, with the constituents which are, for example, part of the composition of paint.

Molecules of mercaptan type have been widely used for many decades in the polymer industry as chain transfer agents in free-radical polymerization. The use of a transfer agent of mercaptan type in free-radical polymerization makes it possible to reduce the average size of the polymer chains, and also, in certain cases, to reduce their polymolecularity index. These transfer agents can be used in bulk polymerizations, in homogeneous or dispersed solvent-based media.

However, mercaptans, which are sulfur-containing molecules, can have the disadvantage of being odorous and, in certain cases, toxic. The handling and use thereof are thus made difficult, requiring specific measures for protection of the personnel and equipment using these sulfur-containing compounds, not to mention the always increasing numerous legislation and regulations which prohibit the use of molecules that are toxic and harmful to humans and to the environment.

Many molecules comprising a mercaptan group have been widely described in the literature. For example, U.S. Pat. No. 2,281,613 discloses the use of isohexylmercaptan, of octadecylmercaptan and of dodecylmercaptan as transfer agents in the emulsion (co)polymerization of 1,3-butadiene and of 1,3-butadiene derivatives.

U.S. Pat. No. 2,497,107 discloses the use of mercapto-ethyl esters of carboxylic acid in the emulsion copolymerization of isoprene or of butadiene in the presence of α-methylstyrene, of styrene and of acrylonitrile.

U.S. Pat. No. 4,593,081 discloses the use of alkyl 3-mercaptopropionates in the emulsion copolymerization of acrylic monomers.

However, these known chain transfer agents all have one or more drawbacks, such as toxicity, noxiousness, unpleasant odor, lack of effectiveness, in terms of polymerization quality and yield, to mention only the main ones.

There therefore remains a need for chain transfer agents which do not have the drawbacks described above.

Surprisingly, the inventors have discovered, after various experiments and manipulations, that mercapto-methyl esters of certain specific carboxylic acids, used as chain transfer agents in free-radical emulsion polymerization processes, make it possible to prepare polymers and copolymers with improved properties, in particular with a lower molar mass and a narrower distribution than the polymers obtained with the mercapto-ethyl esters of homologous carboxylic acids.

Another advantage associated with the use of the mercapto-methyl esters of carboxylic acids according to the present invention lies in the fact that these mercapto-esters can be obtained from renewable raw materials and in particular from raw materials of vegetable origin.

In addition, these mercapto-esters, which will be defined later, also have the advantage of not being odorous, or being weakly odorous, and do not require particular precautions during uses thereof.

According to a first aspect, the present invention thus relates to the use, as a chain transfer agent in a free-radical emulsion polymerization process of at least one mercapto-methyl ester of a carboxylic acid, represented by formula (1) below:

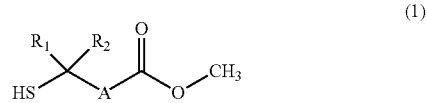

in which:
$R_1$ and $R_2$, which may be identical or different, are chosen, independently of one another, from a hydrogen atom and a linear, branched or cyclic, saturated or unsaturated hydrocarbon-based radical comprising from 1 to 20 carbon atoms, and optionally substituted with one or more radicals chosen from carboxy, alkylcarbonyl and alkoxycarbonyl (where alkyl and alkoxy comprise from 1 to 10 carbon atoms); and A represents a linear, branched or cyclic, saturated or unsaturated, hydrocarbon-based divalent chain comprising from 2 to 30 carbon atoms, limits included, optionally interrupted with one or more heteroatoms chosen from oxygen, sulfur and nitrogen.

According to a first embodiment of the invention, the compounds of formula (1) for which $R_1$ and $R_2$ are identical and each represent a hydrogen atom (primary mercaptans) are preferred.

According to another embodiment, the use according to the invention uses at least one compound of formula (1) in which $R_1$ represents a hydrogen atom and $R_2$ represents a linear, branched or cyclic, saturated or unsaturated hydrocarbon-based radical comprising from 1 to 20 carbon atoms, and optionally substituted as defined previously (secondary mercaptans).

According to yet another embodiment, in the compound of formula (1), $R_1$ and $R_2$, which may be identical or different, each represent a linear, branched or cyclic, saturated or unsaturated hydrocarbon-based radical, comprising from 1 to 20 carbon atoms, and optionally substituted as defined previously (tertiary mercaptans).

In the context of the present invention, preference is given to the mercapto-methyl esters of carboxylic acids comprising a primary mercaptan chain, and then those comprising a secondary mercaptan chain and, finally, those comprising a tertiary mercaptan chain.

In the case of the compounds of formula (1) comprising a secondary or tertiary mercaptan chain, preference is given to those for which the hydrocarbon-based radicals (forming $R_2$ or $R_1$ and $R_2$ respectively) are hydrocarbon-based radicals comprising from 1 to 20 carbon atoms, preferably from 1 to 10 carbon atoms, and more preferably from 1 to 6 carbon atoms. The hydrocarbon-based radicals are chosen from radicals which are linear, branched or cyclic, preferably linear, and saturated or unsaturated, preferably saturated.

Among the preferred substituents of these hydrocarbon-based radicals, mention may be made of substituents of alkoxycarbonyl type, where alkoxy comprises from 1 to 10 carbon atoms, preferably from 1 to 6 carbon atoms, and more preferably from 1 to 4 carbon atoms, and for example alkoxy represents methyl, ethyl, n-propyl, i-propyl, n-butyl, i-butyl or t-butyl. The compounds of formula (1) for which at least one of the radicals $R_1$ or $R_2$ is substituted with a methoxycarbonyl group are particularly preferred.

According to another preferred embodiment, the divalent chain A comprises from 3 to 30 carbon atoms, more preferably from 4 to 30 carbon atoms, and more particularly from 5 to 30 carbon atoms, limits included. The divalent chain A of the compounds of formula (1) may be saturated or totally or partially unsaturated, linear, branched or cyclic, and interrupted with one or more heteroatoms chosen from O, S and N, or even be interrupted with one or more cycles or heterocycles, themselves saturated or totally or partially unsaturated. The divalent chains A which do not comprise heteroatoms, i.e. the divalent chains A which are hydrocarbon-based divalent radicals, optionally comprising one or more unsaturations in the form of double and/or triple bond(s), are preferred.

Nonlimiting examples of divalent chain A which may be mentioned include $—(CH_2)_n—$ chains, or $—(CH_2)_{n1}—C≡C—(CH_2)_{n2}—$ chains, where n represents an integer between 2 and 30 carbon atoms, preferably between 3 and 30 carbon atoms, more preferably between 4 and 30 carbon atoms, and typically between 5 and 30 carbon atoms, limits included, and $n_1+n_2$ is equal to n−2.

Among the compounds of formula (1), those in which $R_1$ and $R_2$ are identical or different and each represent a hydrogen atom or a hydrocarbon-based group and A is as defined previously, are preferred.

According to one particularly preferred embodiment, the compounds of formula (1) are those for which A represents a linear hydrocarbon-based divalent radical comprising from 3 to 18 carbon atoms, more preferably from 4 to 18 carbon atoms, and more preferentially from 6 to 18 carbon atoms, limits included. Particularly preferred representatives are thus methyl mercaptoundecanoate, methyl mercaptodecanoate and dimethyl 9-mercaptooctadecyl-1,18-dioate, preferably methyl mercaptoundecanoate and methyl mercaptodecanoate, and more preferably methyl mercaptodecanoate.

The compounds of formula (1) described above can easily be prepared from the corresponding unsaturated precursor methyl ester which is used in a sulfhydration reaction according to techniques known to those skilled in the art. The term "sulfhydration reaction" is intended to mean the Markovnikov reaction of free-radical addition of H—S—H to a C═C double bond, according to the following scheme:

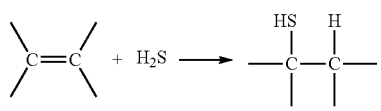

The term "unsaturated precursor methyl ester" is intended to mean a methyl ester comprising at least one double bond capable of being sulfhydrated in one or two steps according to a conventional free-radical addition reaction via the action of hydrogen sulfide (as described, for example, in FR 2 424 907) or of a precursor of hydrogen sulfide, for example thioacetic acid (as described, for example, in U.S. Pat. No. 4,701,492), a tertiary mercaptan, for example tert-butylmercaptan (as described, for example, in FR 2 603 889), or via a catalytic addition of hydrogen sulfide (as described, for example in U.S. Pat. No. 4,102,931).

Thus, the sulfhydration agent used for the sulfhydration of the unsaturated methyl ester to give a compound of formula (1) may be of any type known to those skilled in the art and, for example, chosen from hydrogen sulfide, thioacetic acid (TAA), and other compounds known to those skilled in the art and normally used in organic-compound sulfhydration reactions.

This sulfhydration reaction is advantageously carried out in the presence of homogeneous or heterogeneous acid catalyst and/or under ultraviolet (UV) light irradiation (either by direct photolysis at wavelengths of between 180 nm and 300 nm, or in the presence of photoinitiators). According to one preferred embodiment, the sulfhydration reaction is carried out without catalyst, and under UV irradiation.

This sulfhydration reaction can be carried out in the presence or in the absence of solvent, preferably in the presence of one or more solvents which can be advantageously chosen for their transparency to UV light according to the wavelength used and the ease with which they are separated from the reaction medium. Such solvents can, for example, be chosen from light alkanes (1 to 6 carbon atoms), ethylene glycol ethers, aromatic hydrocarbons, aliphatic hydrocarbons, and the like, and also mixtures of two or more of them in any proportions.

As a variant, the sulfhydration reaction can be carried out in the presence of one or more, preferably one, compound(s) capable of forming free radicals. Such compounds are known to those skilled in the art and can be chosen, for example, from peroxides, and by way of nonlimiting indication, from hydrogen peroxide, sodium peroxide or potassium peroxide, tert-alkyl (for example tert-butyl) hydroperoxides, tert-alkyl peroxides, tert-alkyl peresters, cumene hydroperoxide, azobisisobutyronitrile, and the like, and mixtures of two or more of them in any proportions.

When the sulfhydration reaction described above is carried out via the action of thioacetic acid in the presence of a free-radical initiator and/or by irradiation with UV light, as described previously, this reaction is followed by a methanolysis reaction in acid medium, making it possible to free the desired mercaptan of formula (1). This methanolysis reaction is well known and can be carried out according to any conventional techniques.

At the end of the sulfhydration step, the mercapto-esters can be obtained in the form of mixtures of isomers (primary, secondary and/or tertiary mercaptans) which can be subsequently separated and optionally purified according to conventional separation and/or purification techniques, for example by distillation, under atmospheric pressure or under reduced pressure depending on the nature of the mercaptan of interest to be recovered.

The precursor methyl esters comprising at least one double bond capable of being sulfhydrated using a sulfhydration reagent are known and commercially available or else can be prepared according to any methods and procedures known to those skilled in the art and available in the patent literature, the scientific literature or Chemical Abstracts or else on the Internet.

According to one embodiment, the precursor methyl esters comprising at least one double bond capable of being sulfhydrated can be obtained by transesterification of glycerides (mono-, di- or triglycerides, preferably triglycerides) with methanol, according to conventional methods known to those skilled in the art and, for example, according to the process described in EP-B-0 658 183. The unsaturated glycerides which can be used originate essentially from animal or vegetable, preferably vegetable, oils or fats, among which mention may be made, by way of nonlimiting indication, of soybean oil, sunflower oil, linseed oil, rapeseed oil, castor oil, palm oil, palm kernel oil, coconut oil, jatropha oil, cottonseed oil, peanut oil, olive oil, Vernonia oil, Cuphea oil, Hevea oil, Honesty oil, safflower oil, camelina oil, *Calophyllum inophyllum* oil, *Pongamia pinnata* oil, beef tallow, cooking oil or fat, but can also be hydraulic or lubricating oils.

According to another embodiment, the precursor methyl esters of the compounds of formula (1) can also be obtained by cross-metathesis from other methyl esters, or even from glycerides (the latter will subsequently be subjected to a transesterification step with methanol), for instance those defined previously. The metathesis reactions are well known to those skilled in the art and most commonly call for an intermolecular reaction between two compounds each bearing at least one double bond, as described, for example, in international application WO 2009/047444.

In particular, the compounds of formula (1) in which $R_1$, or $R_1$ and $R_2$, represent(s) a hydrocarbon-based radical substituted with an alkoxycarbonyl radical (di- and triesters, respectively) can advantageously be obtained by metathesis from unsaturated monoesters, according to metathesis techniques known to those skilled in the art. Examples of unsaturated methyl esters which can be used in a metathesis reaction in order to produce di- and triesters include methyl oleate, methyl palmitoleate and methyl arachidonate, alone or as mixtures of two or more of them in any proportions. According to this embodiment, dimethyl 9-octadecene-1,18-dioate can, for example, be readily obtained by metathesis of methyl oleate and/or of methyl palmitoleate.

The sources of methyl esters of formula (1) are thus very numerous and varied, and examples, given by way of nonlimiting indication, of methyl esters bearing an unsaturation capable of being sulfhydrated include, in an indicative and nonlimiting manner, methyl hexenoates, methyl decenoates, methyl undecenoates, methyl dodecenoates, methyl oleate, methyl linoleate, methyl myristoleate, methyl palmitoleate, methyl linoleate, methyl linolenate, methyl arachidonate, methyl ricinoleate and dimethyl 9-octadecene-1,18-dioate, and also mixtures of two or more of them in any proportions.

Preferably, the unsaturated methyl esters are chosen from methyl decenoates and methyl undecenoates, more preferably from methyl decen-9-oate and methyl undecen-10-oate.

As a variant, the precursor methyl esters of the compounds of formula (1) can also be obtained from the corresponding acids, which are subjected to an esterification reaction with methanol according to conventional esterification techniques well known to those skilled in the art.

Examples, given by way of nonlimiting indication, of methyl ester precursor acids include, in a nonlimiting manner, hexenoic acids, decenoic acids, undecenoic acids, dodecenoic acids, oleic acid, linoleic acid, myristic acid, palmitic acid, linoleic acid, linolenic acid, arachidonic acid, ricinoleic acid, diacids and triacids which can be obtained by cross-metathesis according to conventional methods of synthesis by metathesis, as indicated above, and for example 9-octadecene-1,18-dioic acid. Preferably, said acids are chosen from decenoic acids and undecenoic acids and mixtures of two or more of them in any proportions, more preferably from decen-9-oic acid and undecen-10-oic acid.

Among the compounds of formula (1), preference is given to the compounds for which $R_1$ represents a linear, branched or cyclic, saturated or unsaturated hydrocarbon-based radical comprising from 1 to 20 carbon atoms substituted by one or more alkoxycarbonyl radicals, wherein alkoxy contains from 1 to 10 carbon atoms and $R_2$ represents hydrogen, on the one hand, and $R_1$ and $R_2$, identical or different, each represent a linear, branched or cyclic, saturated or unsaturated hydrocarbon-based radical comprising from 1 to 20 carbon atoms substituted by one or more alkoxycarbonyl radicals, wherein alkoxy contains from 1 to 10 carbon atoms.

Thus and according to another aspect, the present invention relates to the compounds of formula (1') below:

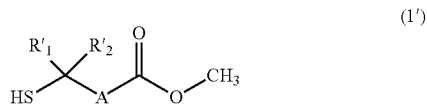

in which:
  $R'_1$ represents a linear, branched or cyclic, saturated or unsaturated hydrocarbon-based radical comprising from 1 to 20 carbon atoms, substituted with one or more alkoxycarbonyl radicals, where alkoxy comprises from 1 to 10 carbon atoms;
  $R'_2$ is chosen from a hydrogen atom and a linear, branched or cyclic, saturated or unsaturated hydrocarbon-based radical comprising from 1 to 20 carbon atoms, substituted with one or more alkoxycarbonyl radicals, where alkoxy comprises from 1 to 10 carbon atoms; and
  A represents a linear, branched or cyclic, saturated or unsaturated, hydrocarbon-based divalent chain comprising from 2 to 30 carbon atoms, limits included, optionally interrupted with one or more heteroatoms chosen from oxygen, sulfur and nitrogen.

The compounds of formula (1') form a subset of the compounds of formula (1), all of the compounds of formula (1') being included in general formula (1). The compounds of formula (1') for which $R'_1$ represents a linear, branched or cyclic, saturated or unsaturated hydrocarbon-based radical comprising from 1 to 20 carbon atoms, substituted with a methoxycarbonyl radical, $R'_2$ represents a hydrogen atom, and A is as defined previously, are preferred.

An example of an unsaturated mercapto diester of formula (1') is represented by dimethyl 9-mercaptooctadecyl-1,18-dioate.

According to the present invention, the mercapto-esters of formula (1) have entirely advantageous applications in the field of polymer synthesis as chain transfer agents.

Thus, the invention also relates to an emulsion (co)polymerization process comprising the formation of an emulsion in water of at least one monomer with at least one mercapto-ester of formula (1) as chain transfer agent.

More specifically, the invention relates to an emulsion (co) polymerization process, comprising at least the following steps:
a) forming an emulsion, in an aqueous medium, of at least one monomer containing vinyl unsaturation,
b) adding to said emulsion at least one chain transfer agent of formula (1) as defined previously,
c) carrying out the (co)polymerization reaction, optionally in the presence of a (co)polymerization initiator,
d) optionally purifying and recovering the desired (co)polymer.

In the (co)polymerization process according to the invention, the amount of chain transfer agent(s) of formula (1) is generally between 0.01% and 5% by weight, preferably between 0.03% and 3% by weight, relative to the total weight of the emulsion.

As regards the amount of monomer(s), it is most commonly between 10% and 60% by weight, preferably between 20% and 50% by weight, relative to the total weight of the emulsion.

The monomers which can be used in the (co)polymerization process according to the invention are the monomers commonly and normally used in free-radical emulsion polymerization reaction, and advantageously the monomers referred to as containing vinyl unsaturation(s), and more particularly vinyl monomers, conjugated diene monomers, acrylic monomers, methacrylic monomers, and mixtures of two or more of them in any proportions, to mention only the most common of them.

In one embodiment of the process according to the invention, nonlimiting examples of monomers comprise acrylic acid, alkyl acrylates, methacrylic acid, alkyl methacrylates, conjugated dienes, styrene and styrene derivatives, acrylamide, acrylonitrile, and also mixtures of two or more of them in any proportions.

According to one preferred embodiment, the monomers are chosen from:
acrylic acid,
methyl acrylate, ethyl acrylate, n-propyl acrylate, iso-propyl acrylate, n-butyl acrylate, iso-butyl acrylate, tert-butyl acrylate, n-pentyl acrylate, neo-pentyl acrylate, iso-amyl acrylate, n-hexyl acrylate, iso-hexyl acrylate, cyclohexyl acrylate, iso-octyl acrylate, 2-ethylhexyl acrylate, decyl acrylate, iso-decyl acrylate, lauryl acrylate, stearyl acrylate and iso-bornyl acrylate, and mixtures thereof,
methacrylic acid,
methyl methacrylate, ethyl methacrylate, n-propyl methacrylate, iso-propyl methacrylate, n-butyl methacrylate, iso-butyl methacrylate, tert-butyl methacrylate, n-pentyl methacrylate, neo-pentyl methacrylate, iso-amyl methacrylate, n-hexyl methacrylate, iso-hexyl methacrylate, cyclohexyl methacrylate, iso-octyl methacrylate, 2-ethylhexyl methacrylate, decyl methacrylate, iso-decyl methacrylate, lauryl methacrylate, stearyl methacrylate, hydroxyethyl methacrylate, hydroxypropyl methacrylate, acetoxyethyl methacrylate, acetoxypropyl methacrylate, tert-butylaminoethyl methacrylate, 2-(3-oxazolidinyl)ethyl methacrylate, iso-bornyl methacrylate, and the like, and mixtures thereof,
acrylonitrile, methacrylonitrile, acrylamide and methacrylamide, and mixtures thereof,
allylacetoacetates, ethylene, propylene, styrene and substituted styrenes, butadiene, vinyl acetate, vinyl versatate, vinyl butyrates and other vinyl esters, halogenated vinyl monomers, such as vinyl chloride, vinylidene chloride, and the like, and mixtures thereof.

The monomeric compounds listed above can of course be used alone or as mixtures, for example as mixtures of two or more of them in any proportions. When two or more monomers are used in the process of the present invention, this results in a copolymer; when a single monomer is used in the process of the present invention, this results in a homopolymer. The copolymers and homopolymers are grouped together under the generic term (co)polymers in the description of the present invention.

The copolymers can be obtained in the form of random, block or alternating copolymers, depending on the operating conditions of the copolymerization process, which conditions are well known to those skilled in the art.

The (co)polymerization reaction medium can also comprise at least one surfactant and/or at least one polymerization initiator and/or at least one chain-terminating agent.

In one embodiment of the present invention, the surfactant(s) used can be chosen from anionic surfactant(s) and/or non-ionic surfactant(s), such as alkyl, aryl or alkylaryl sulfates, sulfonates or phosphates of alkali metals or the corresponding ammonium salts. Surfactants such as alkylsulfonic acids, sulfosuccinate salts, fatty acid salts, ethoxylated alcohols, amphiphilic copolymers, and also mixtures of two or more of them, can also be used.

In general, the amount of surfactant(s) depends on the concentration of monomer(s) in the emulsion, and on the nature of the monomer(s), and most commonly is between 0.05% and 10% by weight, relative to the total weight of the emulsion.

The emulsion (co)polymerization of monomers according to the invention can be initiated by free-radical initiators of any type, generally of oxidizing type, known to those skilled in the art, such as, in a nonlimiting manner, hydrogen peroxide, sodium peroxide, potassium peroxide, tert-butyl hydroperoxide and tert-alkyl hydroperoxides in general, tert-alkyl peroxides, tert-alkyl peresters, cumene hydroperoxide, ammonium or alkali metal persulfates, alkali metal perborates (for example sodium perborate), perphosphoric acid and associated salts thereof, potassium permanganate, ammonium or alkali metal salts of peroxydisulfuric acids, and also mixtures of two or more of them.

For initiation of the reaction by oxidation-reduction, at least one oxidizing agent chosen from those listed above can be used in combination with a reducing agent such as ascorbic acid, iso-ascorbic acid, sodium formaldehyde sulfoxylate, sodium sulfite, sodium bisulfite, sodium thiosulfate, sodium hydrosulfite, sodium sulfide, sodium hydrosulfide or dithiosulfate, formamidinesulfonic acid, hydroxymethanesulfonic acid, sodium 2-hydroxy-2-sulfinatoacetate, acetone bisulfite, ethanolamine, glycolic acid, lactic acid, glyceric acid, malic acid and tartaric acid, and also mixtures of two or more of them.

The oxidation-reduction reactions can themselves be catalyzed by metal salts such as iron, copper, manganese, silver, platinum, vanadium, nickel, chromium, palladium or cobalt salts. These catalysts can be added in contents of between 0.01 ppm and 25 ppm by weight, relative to the total weight of the emulsion.

The amount of (co)polymerization initiator(s) is generally between 0.001% and 1% by weight, relative to the total weight of the emulsion.

The emulsifying phase is generally water or a water/organic solvent(s) mixture, the quantity of which is that which is sufficient (qs) to reach 100% by weight, relative to the total weight of the emulsion.

In one embodiment of the process, the emulsion of monomer(s) comprises between 0.1% and 1% by weight of at least one compound of formula (1), between 20% and 60% by weight of at least one monomer containing vinyl unsaturation(s) defined previously, between 0.1% and 5% by weight of at least one surfactant, between 0.005% and 1% by weight of at least one polymerization initiator, and water in sufficient quantity to reach 100% by weight, relative to the total weight of the emulsion.

According to one embodiment of the process of the invention, the compound of formula (1) can be added continuously or batchwise, either at the beginning of the reaction, or several times during the process, or else continuously throughout the process or throughout a part of the process.

The inventors have discovered, surprisingly, that the free-radical (co)polymerization reaction is controlled all the better, in terms of molar mass and polymolecularity, when it is carried out in the presence of at least one transfer agent of formula (1), i.e. of at least one mercapto-methyl ester, where the mercaptan function is tertiary, secondary or primary, preferably secondary or primary, more preferably primary.

The emulsion according to the invention can be prepared according to the usual techniques well known to those skilled in the art in the field of monomer emulsions. The emulsion process according to the invention can be carried out either batchwise or continuously, and either with a single addition of monomer(s) at the beginning of the reaction, or with one or more continuous or batchwise addition(s) of monomer(s) over time, according to the techniques commonly used in the emulsion field.

Likewise, the polymerization initiator(s) can be added all at once at the beginning of the process, several times during the process, or else continuously throughout the process.

The free-radical (co)polymerization reaction initiation phase can be carried out thermally, photochemically, electrochemically or by oxidation-reduction reaction, or else by any method known to those skilled in the art specializing in this type of reaction.

The reaction for thermally initiating the polymerization is preferentially carried out at a temperature of between 50° C. and 100° C.

The (co)polymerization reaction according to the present invention can itself be carried out at any temperature and any pressure that those skilled in the art will be able to adjust according to the nature and the amount/concentration of the monomers present in the emulsion. Advantageously, the (co)polymerization process of the invention is carried out at atmospheric pressure at a temperature of between 0° C. and 100° C., preferably between 10° C. and 90° C.

The following nonlimiting examples make it possible to illustrate the invention and understand it more clearly.

EXAMPLE 1

Preparation of methyl 10-mercaptodecanoate

9-Decenoic acid (100 g; 0.588 mol) is added to 237 g (300 ml; 7.406 mol) of methanol and the mixture is brought to reflux, with stirring in the presence of 10 g of wet Amberlyst® 15 cation exchange resin. The assembly uses continuous drying of the methanol by passing over a Soxhlet apparatus loaded with molecular sieve (30 g). After 24 hours at reflux and elimination of the solvent under vacuum, the degree of conversion of the acid to ester is close to 99%.

The resulting methyl 9-decenoate (156 g) is placed in a photochemical reactor comprising a reaction loop, with 100 g of pentane and 60 molar equivalents of liquefied hydrogen sulfide (1806 g condensed at 20° C. under a pressure of 17.5 bar).

The mixture is recirculated (60 l/h) in the reaction loop within which it is subjected to UV radiation (wavelength: 254 nm, power: 12 watts) for 3 hours at a temperature of 38° C. and a pressure of 23 bar.

The excess hydrogen sulfide is then flushed to a thermal oxidizer by decompression of the medium, and then by stripping with nitrogen. The mixture is then distilled in order to eliminate the solvent and the sulfides formed (T: 130° C., pressure: 5 mbar).

The resulting mercaptan has a purity greater than 98.5% (measured by chromatography). The amount of primary mercaptan obtained is 97.7%, and the amount of secondary mercaptan obtained is 2.3%, these percentages being percentages by weight relative to the total weight of mercaptans obtained.

EXAMPLE 2

Preparation of methyl 11-mercaptoundecanoate

Methyl 11-mercaptoundecanoate is prepared according to a procedure similar to that described in Example 1 above, using methyl 10-undecenoate.

EXAMPLES 3 TO 8

Emulsion polymerization 40 g of butyl acrylate (Aldrich), 40 g of methyl methacrylate (Arkema), 0.04 g of potassium persulfate (Aldrich), 2.4 g of Dowfax2A1 surfactant (Dow), 0.04 g of sodium hydrogen carbonate (buffer, Aldrich), 332 g of demineralized water and 0.4 g of chain transfer agent according to the present invention are added to a refrigerated jacketed reactor equipped with a stirrer motor and a reflux condenser.

The monomer emulsion is heated at a temperature of between 70° C. and 75° C. for 5 hours.

The polymerization reaction is stopped when the solids content reaches 20% by weight. The solids content is measured by means of a Mettler thermobalance at a temperature of 105° C.

The analysis of the polymers by size exclusion chromatography is carried out in tetrahydrofuran (THF) at 40° C. at 0.3 g/l with a flow rate of 1 ml/min., on a set of MIXED A gel permeation columns (Plgel) (30 cm) with a refractometric detector. The columns are calibrated with a poly(methyl methacrylate) standard.

This analysis by size exclusion chromatography allows for the determination of the mean weight molar mass (Mw) and the mean number molar mass (Mn). The polymolecularity index is calculated as the ratio MW/Mn. The results are given in the following Table 1:

TABLE 1

| Example | Chain transfer agent | Molar mass (Mw) (kg/mol) | Poly-molecularity index |
|---|---|---|---|
| 3 | Methyl 11-mercaptoundecanoate | 129 | 2.6 |
| 4 | Methyl 10-mercaptodecanoate | 105 | 2.5 |
| 5* | n-Dodecylmercaptan | 140 | 4 |
| 6* | tert-Dodecylmercaptan | 381 | 9.3 |
| 7* | Ethyl 11-mercaptoundecanoate | 161 | 3 |
| 8* | Mercaptoundecanoic acid | 1200 | 4.4 |

*indicates the comparative examples

Examples 3 to 8 above are examples of preparation of butyl acrylate/methyl methacrylate copolymer with identical operating conditions, except for the transfer agents used.

The copolymerizations of Examples 3 and 4 are carried out with the chain transfer agents according to the invention. In Examples 5 and 6 (comparative), the chain transfer agents are linear-chain and branched-chain mercaptans, respectively, and are available from Arkema. In Example 7 (comparative), the chain transfer agent was prepared according to a procedure similar to that used to prepare the chain transfer agents according to the invention from 10-decenoic acid subjected to an esterification reaction with ethanol. Finally, in Example 8 (comparative), the transfer agent used is a mercapto-acid available from Aldrich.

The results in Table 1 above show that the chain transfer agents according to the present invention are particularly suitable for emulsion preparation of (co)polymers. Indeed, the (co)polymers obtained not only have sizes (Mw) which are entirely in accordance with those of the copolymers obtained with chain transfer agents conventionally used in the prior art, or even smaller sizes, but also and especially have polymolecularity indices which are very low and significantly lower than those obtained with the chain transfer agents of mercapto-ethyl ester type, which are nevertheless structurally close.

The use of chain transfer agents according to the invention thus makes it possible to prepare (co)polymers of which the properties in terms of molecular weight and of polymolecularity are entirely unexpected from the viewpoint of the prior art. This makes it possible to envisage the use of these (co)polymers in specific applications requiring polymers with a low polymolecularity index, for example in the fields of paints and coatings in general, adhesives, coating of paper, lubrication additives, and the like.

The invention claimed is:

1. A free-radical emulsion polymerization process, comprising: introducing, as a chain transfer agent, at least one mercapto-methyl ester of a carboxylic acid, of formula (1):

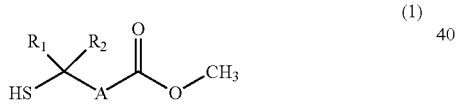

(1)

in which:
R$_1$ and R$_2$, which may be identical or different, are chosen, independently of one another, from a hydrogen atom and a linear, branched or cyclic, saturated or unsaturated hydrocarbon-based radical comprising from 1 to 20 carbon atoms, and optionally substituted with one or more radicals chosen from carboxy, alkylcarbonyl and alkoxycarbonyl (where alkyl and alkoxy comprise from 1 to 10 carbon atoms); and
A represents a linear, branched or cyclic, saturated or unsaturated, hydrocarbon-based divalent chain comprising from 2 to 30 carbon atoms, limits included, optionally interrupted with one or more heteroatoms chosen from oxygen, sulfur and nitrogen.

2. The process according to claim 1, in which R$_1$ and R$_2$ each represent a hydrogen atom.

3. The process according to claim 1, in which A is a —(CH$_2$)$_n$— chain, or a —(CH$_2$)$_{n1}$—C=C—(CH$_2$)$_{n2}$— chain, where n represents an integer between 2 and 30 carbon atoms, limits included, and n$_1$+n$_2$ is equal to n−2.

4. The process according to any one of the preceding claims, in which the compound of formula (1) is methyl mercaptoundecanoate or methyl mercaptodecanoate.

5. Compound of formula (1'):

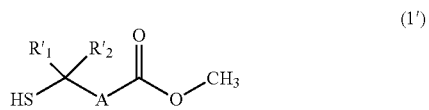

(1')

in which:
R'$_1$ represents a linear, branched or cyclic, saturated or unsaturated hydrocarbon-based radical comprising from 1 to 20 carbon atoms, substituted with one or more alkoxycarbonyl radicals, where alkoxy comprises from 1 to 10 carbon atoms;
R'$_2$ is chosen from a hydrogen atom and a linear, branched or cyclic, saturated or unsaturated hydrocarbon-based radical comprising from 1 to 20 carbon atoms, substituted with one or more alkoxycarbonyl radicals, where alkoxy comprises from 1 to 10 carbon atoms; and
A represents a linear, branched or cyclic, saturated or unsaturated, hydrocarbon-based divalent chain comprising from 2 to 30 carbon atoms, limits included, optionally interrupted with one or more heteroatoms chosen from oxygen, sulfur and nitrogen.

6. Compound according to claim 5, in which R'$_1$ represents a linear, branched or cyclic, saturated or unsaturated hydrocarbon-based radical comprising from 1 to 20 carbon atoms, substituted with a methoxycarbonyl radical, R'$_2$ represents a hydrogen atom, and A is as defined in claim 5.

7. Compound according to claim 5, which is dimethyl 9-mercaptooctadecyl-1,18-dioate.

8. Emulsion (co)polymerization process comprising at least the following steps:
a) forming an emulsion, in an aqueous medium, of at least one monomer containing vinyl unsaturation,
b) adding to said emulsion at least one chain transfer agent of formula (1) according to claim 1,
c) carrying out the (co)polymerization reaction, optionally in the presence of a (co)polymerization initiator,
d) optionally purifying and recovering the desired (co)polymer.

9. Process according to claim 8, in which the amount of chain transfer agent(s) of formula (1) is between 0.01% and 5% by weight, relative to the total weight of the emulsion.

10. Process according to claim 8, in which the monomers containing vinyl unsaturation are vinyl monomers, conjugated diene monomers, acrylic monomers, methacrylic monomers, and mixtures of two or more of them in any proportions.

11. Process according to claim 8, in which the reaction medium also comprises at least one surfactant and/or at least one polymerization initiator and/or at least one chain-terminating agent.

12. The process of claim 3, wherein n represents an integer between 3 and 30 carbon atoms.

13. The process of claim 3, wherein n represents an integer between 4 and 30 carbon atoms.

14. The process of claim 3, wherein n represents an integer between 5 and 30 carbon atoms.

15. The process of claim 4, wherein the compound of formula (1) is methyl mercaptodecanoate.

16. The process of claim 9, wherein the amount of chain transfer agent(s) of formula (1) is between 0.03% and 3% by weight, relative to the total weight of the emulsion.

* * * * *